United States Patent [19]

McAleese

[11] Patent Number: 4,925,567

[45] Date of Patent: May 15, 1990

[54] BASELINE STABIILTY IN GRADIENT ION CHROMATOGRAPHY BY USING A NONIONIC MODIFIER

[75] Inventor: David L. McAleese, Cary, N.C.

[73] Assignee: BASF Corporation, Parsippany, N.J.

[21] Appl. No.: 317,766

[22] Filed: Mar. 2, 1989

[51] Int. Cl.$^5$ .............................................. B01D 15/08
[52] U.S. Cl. ................................. 210/656; 210/198.2; 210/659; 436/150; 436/161; 436/178; 422/70
[58] Field of Search ...................... 210/656, 659, 198.2; 422/70; 436/150, 161, 178

[56] References Cited

U.S. PATENT DOCUMENTS

| | | | |
|---|---|---|---|
| 4,500,431 | 2/1985 | Miyanaga | 210/656 |
| 4,507,390 | 3/1985 | Horiuchi | 210/656 |
| 4,751,189 | 6/1988 | Rocklin | 210/656 |

OTHER PUBLICATIONS

Rocklin, "Gradient Elution in Ion Chromatography," Journal of Chromatography, 411 (1987) pp. 107–119.
Jones, "Gradient Elution of Anion in Single Column Ion Chromatography," Anal. Chem. 1988, 60, pp. 1977–1979.
Small, "Novel Ion Exchange Chromatographic Method Using Conductimetric Detection," Analytical Chemistry, vol. 47, No. 11, Sep. 1975, pp. 1801–1809.
Shintani, "Gradient Anion Chromatography with Hydroxide and Carbonate Eluents Using Simultaneous Conductivity and pH Detection," Anal. Chem. 1987, 59, pp. 802–808.
Dasgupta, "Ion Chromatographic Separation of Anions with Ion Interaction Reagents and an Annular Helical Suppressor", Anal. Chem. 1984, 56, pp. 769–772.
Tarter, "Gradient Elution Ion Chromatographic Determination of Inorganic Anions Using a Continuous Gradient," Anal. Chem. 1984, 56, pp. 1264–1268.
Sundes, "Separation of Sulfite, Sulfate, and Thiosulfate by Ion Chromatography with Gradient Elution," Anal. Chem. 1983, 55, pp. 2–4.

Primary Examiner—Ernest G. Therkorn
Attorney, Agent, or Firm—Rupert B. Hurley, Jr.

[57] ABSTRACT

A stable baseline is achieved in a gradient ion chromatographic analysis by adding a nonionic modifier to the electrolytic eluent. The addition of the modifier may occur at any point upstream of the detector. The nonionic modifier has the effect of shifting the equilibrium of unsuppressed effluent electrolyte towards it nonionic form. For example, the addition of the nonionic modifier shifts both bicarbonate and carbonate towards the nonionic, nonconductive carbonic acid form.

25 Claims, 1 Drawing Sheet

BASELINE STABILITY IN GRADIENT ION CHROMATOGRAPHY BY USING A NONIONIC MODIFIER

BACKGROUND OF THE INVENTION

The present invention pertains to the area of chemical analysis by chromatography. Specifically, the chemical analysis is in the field of liquid chromatography, more specifically ion chromatography and most specifically gradient ion chromatography. Quantitative gradient ion chromatography is known to be a difficult field of analysis because of baseline drift problems encountered from increasing, as a function of time, the ionic strength of the mobile phase. The ionic strength of the mobile phase may be increased by either increasing the concentration of the electrolyte (i.e. the displacing ion) being used, or by switching over to an electrolytic element having a higher ionic strength, or both. If baseline drift is permitted, accurate quantitative analysis of the amounts of late-eluting species is not possible The present invention pertains to a specific means of elimination of baseline drift, thereby permitting gradient ion chromatography to be useful for the quantitative comparison of sample components which vary widely in affinity for the stationary phase within the column.

DESCRIPTION OF THE RELATED ART

U.S. Pat. No. 4,751,189 ('189) describes a method of gradient ion chromatography in which a sample passes through a chromatographic column, a suppressor column, and a conductivity detector. The gradient method utilizes an electrolyte (displacing ion) in the eluent p-Cyanophenate is the electrolyte utilized, and its concentration is increased with time. A nonionic polyhydroxy compound (mannitol) is added to the eluent at a higher concentration at the beginning of the chromatographic run. The concentration of mannitol (which is added to the eluent) is decreased as the run progresses. Boric acid is introduced into the suppressor column at a constant concentration as the run progresses. Both boric acid and mannitol have relatively low conductivities. However, boric acid and mannitol react to form a stronger acid which has a significantly higher conductivity. As the conductivity contributed by p-cyanophenate increases due to the increasing concentration of p-cyanophenate during the chromatographic run, the total conductivity of the effluent is kept constant by decreasing the concentration of the conductive acid formed by the reaction of boric acid and mannitol. The concentration of the conductive acid decreases because the concentration of mannitol is decreased as a function of time. The decrease in mannitol concentration is optimized in order to exactly offset the increase in conductivity produced by the increasing concentration of p-cyanophenate. In this way, the baseline drift is eliminated.

The process of the present invention differs from the process of the '189 patent in several ways. First, the process of the '189 patent generates baseline stability by maintaining a relatively "high" (but constant) baseline conductivity by offsetting the necessary increases in the concentration of the eluent electrolyte (i.e. p-cyanophenate) during the run by decreasing the concentration of a substance (i.e. reaction product of mannitol and boric acid). In stark contrast, the process of the present invention produces a steady baseline at a relatively "low" conductivity level. Also, the present invention does not utilize additional electrolytes to produce a constant baseline conductivity. Rather, the present invention achieves a constant baseline conductivity by shifting the equilibrium of the anion electrolyte (e.g. carbonate and bicarbonate) in the suppressed effluent to its nonionic acid form (e.g. carbonic acid). This eliminates the presence of the effluent electrolyte at the detector It should be noted that where the '189 patent decreases the amount of additive components during the chromatographic run, the process of the present invention preferably increases (or may keep constant) the amount of its additive during the chromatographic run. However, as indicated above, this is only one of several major differences between the process of the present invention and the '189 patent.

Also related to the process of the present invention is Sunden, et. al., "Separation of Sulfite, Sulfate, and Thiosulfate by Ion Chromatography with Gradient Elution", *Analytical Chemistry*, 1983, 55, 2–4. This article describes a gradient ion chromatography process in which the gradient is achieved by substituting sodium carbonate for sodium bicarbonate during the chromatographic run. The sodium carbonate eluent has a higher ionic strength and thereby reduces the elution time for anions having high retention times on the column.

Applicant's claimed process differs from the Sunden article in several important ways. First, whereas the Sunden process has a constant total bicarbonate and carbonate electrolyte concentration during the run, Applicant's claimed process requires that the total bicarbonate and carbonate electrolyte concentration be increased during the run. Sunden's process does not utilize a nonionic modifier, whereas Applicant's claimed process requires the use of a nonionic modifier.

Also related to the process of the present invention is Jones, et. al., "Gradient Elution of Anions in Single Column Ion Chromatography", *Analytical Chemistry*, 1988, 60, 1977–1979. This article describes a technique therein termed "isoconductive gradient" for minimizing background (i.e. baseline) conductivity changes in the mobile phases. This process expressly excludes the use of a suppressor column. The gist of the process in Jones, et. al. is that a weaker-conducting cation may be substituted for a stronger-conducting cation, so that the concentration of the electrolyte may be increased while manipulating the strong:weak cation ratio so that the baseline is constant.

In contrast to the Jones article, Applicant's claimed process:
(1) requires the step of suppressing (whereas Jones states that his method does not require or utilize a suppression step);
(2) shifts the ionic-nonionic balance of the electrolyte present (Jones' process does not attempt to affect the equilibrium condition regarding the electrolyte).

Tarter, J. G., "Gradient Elution Ion Chromatographic Determination of Inorganic Anions Using a Continuous Gradient", *Analytical Chemistry*, 1984, 56, 1264–1268 describes a method of gradient elution solvent delivery wherein the elution begins with a bicarbonate electrolyte and later utilizes a carbonate electrolyte in order to elute components which are retained on the column to a greater degree. Tarter's method is not intended to achieve baseline stability. Tarter does not utilize a nonionic modifier. Furthermore, Tarter refers to the fact that his baseline drifts.

Shintani, H., et. al., "Gradient Anion Chromatography with Hydroxide and Carbonate Eluents Using Simultaneous Conductivity and pH Detection", *Analytical Chemistry*, 1987, 59, 802–808, describes a method for conducting gradient anion chromatography using hydroxide and carbonate eluents. The Shintani method does not employ a nonionic modifier. As can be seen in Shintani's FIGS. 5, 6, and 7, Shintani makes no effort to control baseline drift In FIG. 8, Shintani uses a computer for reducing the baseline drift. Computerized elimination of baseline drift does not eliminate the quantitative uncertainties associated with an elevated baseline, but rather is merely cosmetic in effect. Chemical means of elimination of baseline drift is required in order to ensure reproducible quantitative results.

Dasgupta, P. K., "Ion Chromatographic Separation of Anions with Ion Interaction Reagents and an Annular Helical Suppressor", *Analytical Chemistry*, 1984, 56, 769–772, describes a method of gradient ion chromatography using a sodium hydroxide electrolyte system. The Dasgupta method does not employ a nonionic modifier Furthermore, in FIGS. 2 and 3, Dasgupta's only gradient runs illustrated, Dasgupta obtains baseline elevation. In column 1 of page 771 Dasgupta states that he replaces NPr$_4$OH with NaOH in order to obtain his gradient Rocklin, R. D., et. al., "Gradient Elution in Ion Chromatography", *Journal of Chromatography*, 411 (1987), 107–119, is a survey article on gradient ion chromatography. Rocklin states that severe baseline shifts make gradient ion chromatography difficult, and that unless steps are taken to minimize baseline shifts, gradient elution cannot be successfully employed Rocklin describes gradient elution as being carried out by changing from a weak to a strong eluent during the run. Rocklin refers to a preference for salts of weak acids (NaOH, borate, p-cyanophenate) Rocklin further states that stronger eluent ions exhibit higher background conductivity following suppression, and therefore are generally not acceptable for gradient elution, and that carbonate-containing eluents are generally not acceptable for gradient elution because the baseline shift is too severe. Rocklin later states that if anion exchange can be accomplished via the method of the '189 patent (i.e. mannitol plus boric acid), then the baseline slope can be minimized.

Small, H., "Novel Ion Exchange Chromatographic Method Using Conductimetric Detection", *Analytical Chemistry*, 47, 1975, 1801–1809, describes ion chromatography in general. However, the Small article nowhere refers to gradient ion chromatography.

BRIEF DESCRIPTION OF THE INVENTION

Figure 1:
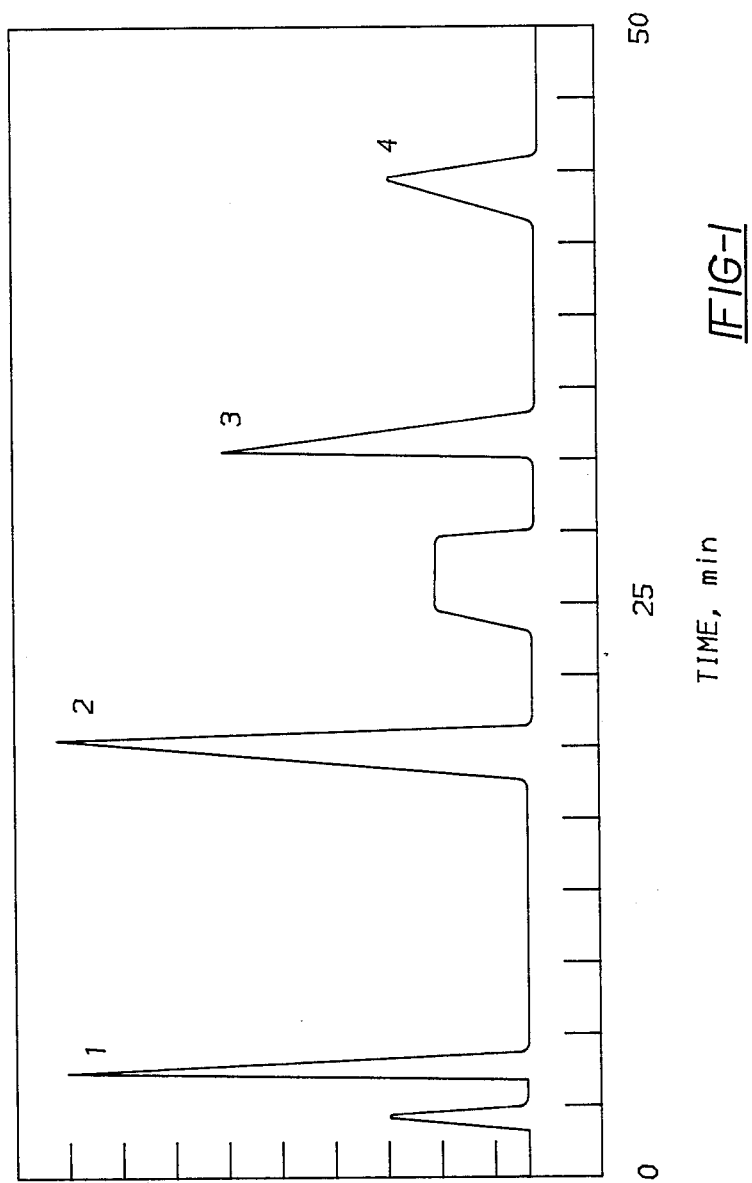
FIG. 1 illustrates the separation of fluoride, chloride, phosphate, and sulphate ions using the step-gradient ion chromatographic method of the present invention.

Gradient ion chromatography requires the use of a suppressor column in order to permit detection of the ions of interest. Without suppression of the effluent electrolyte, the detector (e.g. conductivity detector) will not be able to distinguish between the ions comprising the electrolyte and the ions comprising the sample components being separated on the upstream chromatographic column. Even after suppression, however, not all of the effluent ions are suppressed. Rather, the electrolyte remains in a state of equilibrium between its original and nonionized forms. Furthermore, for concentration gradients, as the concentration of the electrolyte in the electrolytic eluent is increased during gradient ion chromatography, the level of the "unsuppressed" effluent ions increases as the run progresses. For composition gradients, the ionic strength of the electrolytic eluent and "suppressed" effluent increases as the run progresses. This is the cause of the elevation in the baseline during the progress of the run. It has unexpectedly been found that a nonionic modifier may be added to the electrolytic eluent (at any point prior to the detector) whereby after suppression the nonionic modifier shifts the equilibrium of the electrolyte from the ionic form to the nonionic form. When the nonionic modifier is utilized in conjunction with adequate suppression, it has been found that a stable baseline can be achieved during gradient ion chromatography when using displacing anions considerably stronger than hydroxide (e.g. bicarbonate/carbonate systems).

The present invention pertains to a method of gradient ion chromatography having improved background stability, for analyzing a sample solution which contains a plurality of anions. The method uses a gradient eluent The method involves six steps. First, an electrolytic eluent is flowed through an anion exchange chromatography column. Second, while the electrolytic eluent is flowing through the column, an anion solution (to be analyzed) is injected into the flowing electrolytic eluent. The injection into the electrolytic eluent takes place upstream of the chromatographic column, and the anion solution then passes through the chromatographic column, whereby the anions are separated in the chromatographic column. A valve may be used to inject the anion solution to be analyzed into the flowing electrolytic eluent. Third, during the chromatographic separation the ionic strength of the electrolytic eluent is increased as a function of time. Fourth, an effective amount of a nonionic modifier is added to the electrolytic eluent at a point upstream of the detector, the nonionic modifier being a substantially water-soluble compound which is non-reactive with the electrolytic eluent and which, upon suppression, shifts the ionic-nonionic balance of the electrolytic eluent towards the nonionic form. The shift in balance is controlled so that a substantially balanced baseline results. Fifth, the ionic strength of at least a portion of the effluent from the chromatographic column is suppressed. Sixth, at least a portion of the effluent emitted from the suppressor column is passed through an electronic property detector, whereby the separated anions are detected.

DETAILED DESCRIPTION OF THE PREFERRED EMBODIMENTS

As described above, the present invention pertains to a method of gradient ion chromatography having a stable baseline. The method achieves a stable baseline by adding a nonionic modifier to the electrolytic eluent or effluent before the effluent enters the detector. The nonionic modifier shifts the equilibrium of the electrolyte anion (bicarbonate and/or carbonate) towards a "nonionic" form (i.e. carbonic acid) following suppression. The suppressor column exchanges the cationic portion of the electrolyte for hydrogen. The main effect of the suppressor column is to remove the cationic portion of the electrolyte. Also, the resulting increase in the hydrogen ion concentration shifts the equilibrium towards the nonconductive carbonic acid, via Le Chatelier's Principle. However, the suppressor column is not 100 percent effective, and as a result the substantial increases in electrolyte strength (due to a shift to a stronger electrolyte and/or the use of higher concentrations of electrolyte) utilized in gradient ion chromatography, the baseline shifts upward during the run because the ionic strength of "unsuppressed" ionic effluent increases as the run progresses.

The inventor of the present invention has discovered an additional means of shifting the ionic-nonionic equilibrium of the electrolyte towards its nonconductive nonionic form (e.g. a carbonate-bicarbonate system is shifted in favor of carbonic acid, following suppression). The inventor has found that this shift can be effectuated by the addition of an effective amount of a "nonionic modifier". There are three main characteristics of the nonionic modifier. First, the modifier is essentially nonionic in nature. Although the modifier does not hinder the eluent's ionic strength during the chromatographic separation, the modifier reduces the conductivity of the effluent following suppression. Secondly, the nonionic modifier causes electrolyte anions to combine with the hydrogen ions in solution, whereby the electrolyte anions are shifted more towards their nonionic acid form. Third, the nonionic modifier has no effect on the anion being analyzed for, i.e. the "sample anion".

The nonionic modifier may be any nonionic compound or compounds which exhibits all three of the above characteristics. The nonionic modifier is preferably selected from the group consisting of isopropanol, propanol, methanol, acetonitrile, dimethylformamide, dioxane, and tetrahydrofuran. More preferably the nonionic modifier is selected from the group consisting of isopropanol, propanol, methanol, and acetonitrile, and most preferably the nonionic modifier is isopropanol.

The concentration of the nonionic modifier is preferably increased as a function of time as the chromatographic run progresses. Most preferably the concentration of the nonionic modifier is increased in a stepwise fashion during the chromatographic run. In any event, the nonionic modifier must be added in an "effective amount", i.e. an amount effective to substantially shift the electrolyte anions to their nonionic form following suppression.

As stated above, the process of the present invention pertains to a method of maintaining a stable baseline during gradient ion chromatography. Thus the ionic strength or eluting strength of the eluent increases as the run progresses. Although the concentration of the nonionic modifier may be a constant during the gradient run, during the course of the run it is preferable to increase the concentration of the nonionic modifier between several percent and 200-fold. It is preferable to increase the ionic strength of the eluent by a factor between 2 and 100 during the run. It is more preferred to increase the ionic strength between 5 and 20 during the run. It is also preferred that the concentration of the nonionic modifier and the ionic strength of the electrolytic eluent are increased in stepwise fashion. Either a concentration gradient or a composition gradient may be used. Preferably the ionic strength of the electrolytic eluent is increased during the chromatographic run by adding at least one additional electrolyte to the eluent or by switching from at least one initial electrolyte to at least one final electrolyte. Preferably the initial electrolyte is bicarbonate and the final electrolyte is carbonate. Another method of increasing the ionic strength of the electrolytic eluent is by increasing the concentration of at least one electrolyte in the eluent during the chromatographic run.

The electrolyte or combination of electrolytes in the electrolytic eluent utilized in the process may be selected from any electrolyte of a weak acid known to be useful in ion chromatography. Preferred electrolytes are one or more of the members selected from the group consisting of sodium carbonate, sodium bicarbonate, potassium carbonate, potassium bicarbonate, lithium carbonate, and lithium bicarbonate. The carbonate and bicarbonate anions are most preferred anions because they offer a wide range in eluting strength, particularly when a single chromatographic gradient run begins with a bicarbonate and later shifts to a carbonate/bicarbonate mixture. Preferably the cation utilized in the electrolytic eluent is an alkali metal, more preferably the cation electrolyte is one or more of the members selected from the group consisting of sodium, potassium, and lithium. These alkali metals have relatively small ionic radii and are more efficiently exchanged for hydrogen ions in a continuously regenerated suppressor column.

The method of the present invention is one in which anions are separated via gradient ion chromatography. Thus the column which is utilized to produce the separation is herein termed an "anion exchange chromatographic column". Preferably the anion exchange chromatography column has a polymeric stationary phase with quaternary ammonium anion exchange sites. The anion exchange column may have either an anion exchange silica stationary phase or an anion exchange polymeric stationary phase. Most preferably, the stationary phase is a styrene divinyl benzene copolymer resin with quaternary ammonium anion exchange sites.

The process of the present invention requires the step of suppression. As discussed above, the suppression step exchanges the vast majority of the cation in the electrolyte for hydrogen ions. The suppression step is carried out in a cation exchange suppressor column. Sometimes the effluent emitted by the chromatographic column has simply too much ionic strength for the suppressor column to suppress. In this instance only a portion of the effluent from the chromatographic column is directed into the suppressor column. The suppressor column is preferably a continuously regenerated suppressor column. More preferably, the suppressor column is a continuously regenerated cation exchange fiber suppressor column or a continuously regenerated cation exchange micromembrane suppressor column.

The process of the present invention also requires the step of flowing at least a portion of the effluent emitted from the suppressor column through an electronic property detector, whereby the separated anions are detected. Sometimes it is desirable to split the effluent stream (emitted from the suppressor column) into several streams, each of which passes into a different detector or to another desired apparatus. Thus the process entails flowing "at least a portion" of the effluent emitted from the suppressor column into an electronic property detector. The "electronic property detector" utilized in the process may be any means capable of detecting the presence and amount of the anion being analyzed for. Most preferably the electronic property detector is a conductivity detector. However, other detectors, such as electrochemical detectors or pH detectors may be utilized As shown in Table I (below), baseline conductivity can be made constant, even though there is a stepwise increase in the ionic strength of the electrolytic eluent. Table I indicates that the level of isopropanol added to the eluent is varied so that, for any given set of gradient electrolyte conditions, a constant baseline conductivity is achieved.

EXAMPLE 1

An aqueous standard solution containing fluoride, chloride, phosphate, and sulfate was separated in a single step gradient ion chromatographic run. The separation was performed on a Dionex AS3 column. The composition of the two eluents used, together with the pressure drop associated with each eluent, and the baseline conductivities of the effluents, are shown in Table I (see Gradient No. 1). The eluent pump switched from Eluent No. 1 to Eluent No. 2 nineteen minutes after injection of the sample. Details of the reagents, instrumentation, and chromatographic conditions are given below.

All chemicals were reagent grade. Eluents and standards were prepared with deionized water from a Millipore Milli-Q water purification system. Eluents were also prepared with isopropanol from a Barnstead Water-I solvent purification system.

The liquid chromatography system consisted of a Precision LC-241 autosampler with a 100 uL injection loop, an LDC/Milton Roy CM-4000 gradient pump for the eluent, an LDC/Milton Roy miniPump ® for the suppressor column regenerant solution, a Bio-Rad CM-8 conductivity detector, a Hewlett-Packard 3357 Laboratory Automation System for collection of chromatographic data, and a Hewlett-Packard 7470A printer/plotter.

A Dionex HPIC-AS3 or HPIC-AS1 anion exchange separator column (4.6×250 mm) and a Dionex cation exchange micromembrane suppressor column were employed for gradient work. Aqueous-isopropanolic eluent solutions containing sodium bicarbonate and/or sodium carbonate were helium sparged and pumped at a flow rate of 1.0 mL/min The suppressor column regenerant consisted of an aqueous 0.025 N sulfuric acid solution which was pumped at a flow rate of 4.0 mL/min The conductivity detector was set on the 10 uS scale. The resulting chromatogram of the aqueous standard solution is shown in FIG. 1. The first (unlabeled) peak eluting at about 1.5 minutes represents the system void (i.e. the water peak). Peak 1 represents fluoride, peak 2 chloride, peak 3 phosphate, and peak 4 sulfate. The fluoride and chloride ions were eluted by the bicarbonate eluent, while the phosphate and sulfate ions were eluted by the bicarbonate-carbonate eluent. Table II provides data on the retention time and quantity of each of the ions injected as shown in FIG. 1 It should be noted that the phosphate and sulfate ions would not have been eluted by the initial bicarbonate eluent for several hours. The separation can, therefore, be viewed as two discrete isocratic separations combined into one step gradient run The chromatogram shows the fluoride peak well separated from the system void peak which normally does not occur in isocratic separations of monovalent and divalent anions.

In FIG. 1, the chromatogram shows a broad, hump-like baseline disturbance between the chloride and phosphate peaks. The baseline began shifting approximately 4 minutes after the step change from the bicarbonate eluent (i.e. eluent 1) to the bicarbonate-carbonate eluent (i.e. eluent 2) was initiated, and the baseline was restored to its original conductivity about 5 minutes later. The baseline disturbance was not due to the elution of reagent impurities that could have accumulated on the column from the initial eluent, because the area of the "disturbance peak" did not change as a function of the length of time the column was equilibrated with the initial eluent The disturbance was due to equilibration of the separator and suppressor columns with the second eluent. A pressure drop change from 650 psi to 690 psi occurred simultaneously with the appearance of the baseline disturbance on the chromatogram. A similar baseline disturbance was observed during re-equilibration with the initial eluent.

The effluent conductivities and pressure drops produced by gradients both with and without ispropanol are shown in Table I (i.e. gradients 1 & 2). Note that the pressure drop is significantly less without isopropanol (gradient 2), but the baseline conductivity increased dramatically after switching from the initial bicarbonate eluent to the bicarbonate-carbonate eluent. Since the conductivity detector did not have auto-zero capability and the change in baseline conductivity exceeded the 10 $\mu$S range setting, the gradient run without isopropanol was not even possible from an instrumental viewpoint.

The chromatogram in FIG. 1 was generated on only the third attempt at matching baseline conductivities with two eluents. Beginning with the second eluent and a 1.5 mM sodium bicarbonate concentration for the initial eluent, the level of isopropanol in the initial eluent was optimized. In other gradient work, one of the eluent reservoirs contained an aqueous 10 mM sodium carbonate solution, a second reservoir contained isopropanol, and a third reservoir contained deionized water. After selection of a sodium carbonate concentration for each eluent and an isopropanol concentration for one of the eluents, the level of isopropanol in the other eluent was optimized. A Dionex AS1 column was utilized for these gradients and the chromatographic conditions are given in Table I (gradients 3 and 4). There was an order of magnitude increase in eluent ionic strength during the chromatographic runs, yet the eluents were easily suppressed to equal conductance values. The difference in isopropanol content in the first and second eluents produced a fairly substantial change in pressure drop during the gradient runs. However, there was essentially no difference in the magnitude or duration of the baseline disturbances in all three gradients. It was also observed that these levels of isopropanol had no detrimental effect on column performance. Chromatograms were reproducible from run to run provided that sufficient time was allowed for re-equilibration with the initial eluent.

TABLE I

| Step Gradient Ion Chromatographic Conditions | | | | |
|---|---|---|---|---|
| Gradient No. | Eluent No. | Eluent Composition | Pressure Drop (psi) | Baseline Conductivity (uS) |
| 1 | 1 | 1.5 mM NaHCO$_3$, 37.5% isopropanol | 650 | 4.8 |
|   | 2 | 3.5 mM NaHCO$_3$, 2.7 mM Na$_2$CO$_3$, 50.0% isopropanol | 690 | 4.8 |
| 2 | 1 | 1.5 mM NaHCO$_3$ | 240 | 13.0 |
|   | 2 | 3.5 mM NaHCO$_3$ 2.7 mM NA$_2$CO$_3$ | 240 | 23.5 |
| 3 | 1 | 0.40 mM Na$_2$CO$_3$ 30.0% isopropanol | 480 | 5.0 |
|   | 2 | 4.0 mM Na$_2$CO$_3$, 56.0% isopropanol | 580 | 5.0 |
| 4 | 1 | 0.50 mM Na$_2$CO$_3$, 16.0% isopropanol | 354 | 7.3 |

TABLE I-continued

Step Gradient Ion Chromatographic Conditions

| Gradient No. | Eluent No. | Eluent Composition | Pressure Drop (psi) | Baseline Conductivity (uS) |
|---|---|---|---|---|
| | 2 | 5.0 mM Na$_2$CO$_3$, 45.0% isopropanol | 560 | 7.3 |

TABLE II

| Peak No. | Eluted Ion | Retention Time (min.) | Ion Quantity ($\mu$g) |
|---|---|---|---|
| 1 | fluoride | 4.57 | 0.20 |
| 2 | chloride | 18.14 | 1.0 |
| 3 | phosphate | 32.17 | 2.0 |
| 4 | sulfate | 43.66 | 0.70 |

The embodiments of the invention in which an exclusive privilege or property is claimed are defined as:

1. A method of ion chromatography with improved background stability for analyzing a sample solution containing a plurality of anions and using a gradient eluent, the method comprising:
   A. flowing an electrolytic eluent through an anion exchange chromatographic column;
   B. injecting, into the flowing electrolytic eluent, an anion solution to be analyzed, the injection taking place upstream of the chromatographic column, the anions being separated in the chromatographic column;
   C. increasing the ionic strength of the electrolytic eluent as a function of time during the chromatographic separation;
   D. adding an effective amount of a nonionic modifier to the electrolytic eluent at a point upstream of the detector, the nonionic modifier being a substantially water-soluble compound which is non-reactive with the electrolytic eluent and causes electrolyte anions to combine with hydrogen ions in solution, whereby the electrolyte anions are shifted more towards their nonionic form and which, upon suppression shifts the ionic/nonnionic balance of the electrolytic eluent towards the nonionic form, the shift in balance being controlled so that a substantially balanced baseline results;
   E. suppressing, in a suppressor column, at least a portion of the ionic strength of an effluent from the chromatographic column;
   F. passing at least a portion of the effluent emitted from the suppressor column through an electronic property detector, whereby the separated anions are detected.

2. The method as described in claim 1 wherein the electrolyte in the electrolytic eluent is selected from the group consisting of sodium carbonate, sodium bicarbonate, potassium carbonate, potassium bicarbonate, lithium carbonate, and lithium bicarbonate.

3. The method as described in claim 1 wherein the cation in the electrolytic eluent is a member selected from the group consisting of sodium, potassium, and lithium.

4. The method as described in claim 1 wherein the anion exchange chromatography column has a silica stationary phase with quaternary ammonium anion exchange sites.

5. The method as described in claim 1 wherein the anion exchange chromatography column has a polymeric stationary phase with quaternary ammonium anion exchange sites.

6. The method as described in claim 1 wherein the anion solution to be analyzed is injected into the flowing electrolytic eluent via a valve.

7. The method as described in claim 1 wherein the nonionic modifier is selected from the group consisting of isopropanol, propanol, methanol, acetonitrile, and dimethylformamide, dioxane, and tetrahydrofuran.

8. The method as described in claim 1 wherein the nonionic modifier is selected from the group consisting of isopropanol, propanol, methanol, and acetonitrile.

9. The method as described in claim 1 wherein the nonionic modifier is isopropanol.

10. The method as described in claim 1 wherein during the chromatographic run, the ionic strength of the eluent is increased by a factor between 2 and 100.

11. The method as described in claim 1 wherein during the chromatographic run, the ionic strength of the eluent is increased by a factor between 5 and 20.

12. The method as described in claim 1 wherein during the chromatographic run the concentration of the nonionic modifier is increased between several percent and 200-fold.

13. The method as described in claim 1 wherein the total concentration of bicarbonate and carbonate in the eluent increases during the chromatographic run.

14. The method as described in claim 1 wherein the suppressor column is a continuously regenerated suppressor column.

15. The method as described in claim 14 wherein the suppressor column is a cation exchange fiber suppressor column.

16. The method as described in claim 14 wherein the suppressor column is a cation exchange micromembrane suppressor column.

17. The method as described in claim 1 wherein the electronic property detector is a conductivity detector.

18. The method as described in claim 1 wherein the electronic property detector is selected from the group consisting of conductivity detectors, electrochemical detectors, and pH detectors.

19. The method as described in claim 1 wherein the ionic strength of the electrolytic eluent is increased by increasing the concentration of at least one electrolyte in the eluent during the chromatographic run.

20. The method as described in claim 1 wherein the ionic strength of the electrolytic eluent is increased by adding at least one additional electrolyte to the electrolytic eluent during the chromatographic run.

21. The method as described in claim 1 wherein the concentration of the nonionic modifier is increased as a function of time as the chromatographic run progresses.

22. The method as described in claim 1 wherein the concentration of the nonionic modifier is increased in a stepwise fashion during the chromatographic run.

23. The method as described in claim 1 wherein the electrolytic eluent comprises sodium carbonate and sodium bicarbonate and wherein the nonionic modifier is isopropanol, and wherein the concentration of the nonionic modifier is increased in stepwise fashion and the ionic strength of the electrolytic eluent is increased in stepwise fashion.

24. The method as described in claim 1 wherein the ionic strength of the electrolytic eluent is increased during the run by switching from at least 1 initial electrolyte in the eluent to at least one final electrolyte in the eluent, and wherein the ionic strength of the final electrolytic eluent is substantially greater than the ionic strength of the initial electrolytic eluent.

25. The method as described in claim 24 wherein the initial electrolyte in the eluent is bicarbonate and the final electrolyte in the eluent is carbonate.

* * * * *